United States Patent [19]

Hofmann

[11] Patent Number: 4,911,806

[45] Date of Patent: Mar. 27, 1990

[54] METHOD AND APPARATUS FOR SEPARATING PARTICLES IN LIQUID SUSPENSION UTILIZING OSCILLATING ELECTRIC AND MAGNETIC FIELDS

[75] Inventor: Gunter A. Hofmann, San Diego, Calif.

[73] Assignee: Biotronics, San Diego, Calif.

[21] Appl. No.: 19,582

[22] Filed: Feb. 27, 1987

[51] Int. Cl.[4] .................................... G01N 27/26
[52] U.S. Cl. ........................... 204/180.1; 204/299 R; 204/183.1; 204/182.1
[58] Field of Search ............... 204/299 R, 155, 182.1, 204/180.1, 183.1, 186, 302, 305; 210/222, 223, 695

[56] References Cited

U.S. PATENT DOCUMENTS

| | | | |
|---|---|---|---|
| 3,207,684 | 9/1965 | Dotts, Jr. | 210/222 X |
| 4,326,026 | 1/1980 | Sarkar | 435/2 |

OTHER PUBLICATIONS

Pohl, Herbert A., "The Force on a Neutral Dielectric Object of Biological Interest in Crossed Time-Varying Electric and Magnetic Fields", Journal of Biological Physics 13(3), 1985, pp. 79-80.

"Magnetic Separation in Biotechnology", by Whitesides et al., 1983.

"Separation of Chromosome-Sized DNA Molecules by Pulsed Field Gel Electrophoresis", Van Der Ploeg, 1987.

"The Force on a Neutral Dielectric Object of Biological Interest . . . ", Pohl, Mar. 24, 1986.

*Primary Examiner*—John F. Niebling
*Assistant Examiner*—John S. Starsiak, Jr.
*Attorney, Agent, or Firm*—Baker, Maxham, Jester & Meador

[57] ABSTRACT

Small dielectric particles such as biological cells or DNA molecules are suspended in a quantity of liquid within a container. A pair of spaced apart electrodes are immersed in the liquid and a coil surrounds the region between the electrodes. First and second electric signals are applied to the electrodes and the coil, respectively, to thereby generate substantially orthogonal oscillating electric and magnetic fields which are at the same frequency but approximately ninety degrees out of phase. By selecting the frequency, particles having different polarization relaxation frequencies and sizes will migrate at different velocities and thereby sort into various fractions.

20 Claims, 2 Drawing Sheets

METHOD AND APPARATUS FOR SEPARATING PARTICLES IN LIQUID SUSPENSION UTILIZING OSCILLATING ELECTRIC AND MAGNETIC FIELDS

BACKGROUND OF THE INVENTION

The present invention relates to the separation of biological cells, small dieletric bodies or large molecules suspended in a liquid.

Conventional chemical processes for purification, such as crystallization and distillation, are unsuitable for biological materials. Biological molecules are difficult to separate because they consist of delicate and chemically similar compounds present in dilute suspensions. The task of separating biological cells is even more difficult because they are fragile and tend to aggregate.

It would be desirable to provide an improved technique for separation of large molecules, such as DNA. Such a technique would facilitate clinical diagnosis of pathogenic organisms by determination of the distribution of chromosome-sized DNA molecules, the location of genes responsible for genetic defects by preparing maps of megabase pair DNA regions, and molecular genetic analysis of genomes.

It would further be desirable to provide an improved technique for separating biological cells and subcellular orgonelles. Such a technique would be generally useful in the isolation of certain cell types for clinical evaluation and culture, and in particular, in the isolation of hybird cells from parent cells in the fields of immunology and agriculture, and the isolation of cells containing the end products of fermentation processes, as well as other genetic engineering applications.

Prior techniques for separating biological cells or similar small dielectric bodies have included electrophoresis, centrifugation, dielectrophoresis, filtering, and magnetophoresis. See for example "Methods of Cell Separation", Vol. 1, 2, 3, N. Catsimpoolas, Plenum Press, New York, 1977. U.S. Pat. No. 4,326,026 discloses a flow activated technique for separating live X and Y sperm cells. U.S. Pat. No. 4,578,168 discloses a dielectrophoresis technique for fusing line cells to form viable hybridomas which may be used in the production of monoclonal antibodies.

SUMMARY OF THE INVENTION

It is therefore the primary object of the present invention to provide a method and apparatus for separating particles in liquid suspension.

Another object of the present invention is to provide an improved method and apparatus for separating large molecules such as DNA.

Another object of the present invention is to provide an improved method and apparatus for separating biological cells.

According to the present invention small dielectric particles such as biological cells or DNA molecules are suspended in a quantity of liquid within a container. A pair of spaced apart electrodes are immersed in the liquid and a coil surrounds the region between the electrodes. First and second electric signals are applied to the electrodes and the coil, respectively, to thereby generate substantially orthogonal oscillating electric and magnetic fields which are at the same frequency but approximately ninety degrees out of phase. By selecting the frequency, particles having different polarization relaxation frequencies and sizes will migrate at different velocities and thereby sort into various factions.

DESCRIPTION OF THE PREFERRED EMBODIMENTS

It is known that tissues and cells behave as dielectric objects when subjected to electric fields. An externally applied electric field is thought to polarize cells through five possible mechanisms, namely, (1) electron-versus-nucleus shift; (2) shift of charged atoms of the molecules with respect to each other; (3) orientation of intrinsic dipoles; (4) polarization due to free charges; and (5) interfacial polarization due to the presence of cell membrane and ionic double layer at the surface. A cellular dipole moment is induced, $$P = \chi \times E, \quad (1)$$

where P is the dipole moment, $\chi$ is the polarizability of the cell and E is the strength of the electric field. The magnitude of $\chi$ is determined by the physical properties of the cell.

In oscillating electric (AC) fields, $\chi$ exhibits pronounced frequency dependence with characteristic relaxation frequencies for each cell type, reflecting the length of response time (relaxation time) required for polarization. Exploitation of this polarizable nature of the cells has already led to the application of electrofusion in hybrid production. My invention provides a method and apparatus for separating cells of different sizes and relaxation frequencies by utilizing oscillating electric and magnetic fields.

Cells are spheres of radius a, homogeneous in size and electric properties. They are suspended in a non-conducting liquid medium of much lower dielectric constant. The electric field in medium is considered not distorted except at the vicinity of the cell membrane. At low cell concentrations, intercellular interaction can be neglected. A single relaxation mechanism of relaxation time $\tau$ and first order reaction is in operation.

The Laplace equation yields:

$$\chi = 4a^3 \pi \epsilon_o \frac{\epsilon - 1}{\epsilon + 2} = 4\pi \epsilon_o a^3 K \quad (2)$$

where $\epsilon_o$=dielectric constant of space and $\epsilon$=ratio of the relative dielectric constants of the cells to the surrounding medium.

The change in the cellular dipole moment with time is related to the electric field in the following fashion:

$$dP/dt = \frac{1}{\tau}(\chi E - P). \quad (3)$$

With an oscillating electric field $E(t) = E_o \cos\omega t$, Equation (3) can be integrated to yield:

$$P(t) = -\frac{2\pi\epsilon_o a^3 k}{1 + (\omega\tau)^2} E (\cos\omega t + \omega t \sin\omega t) \quad (4)$$

Figures 2A, 2B, 2C:
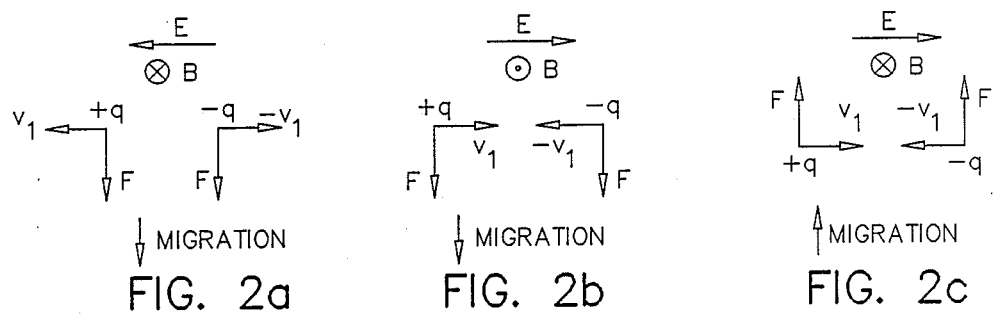
FIGS. 2a, 2b and 2c are a sequence of schematic drawings illustrating the electric field E, magnetic field B, charges +q and −q, velocities +v and −v, and force F involved in performing the method of the present invention.

From an operational point of view, P may be considered a dipole consisting of two opposite charges +q and −q separated at a distance s; P=q.s. For a given system the number of charges generated by polarization is constant (dq/dt=0) and the positions of the two charges are not. By choosing a reference frame centered at the mid point between the two charges, =q and −q are oscillating n opposite directions with velocity of $v_1 = \frac{1}{2}(ds/dt)$ parallel to E. In the presence of an external magnetic field B, forces of the same direction and magnitude $F = q(v_1 \times B)$ are acted on both charges (FIG. 2a). Therefore the dipole, and thus the cell, moves under a force of 2F in the direction perpendicular to both E and B. When E changes direction, so do $v_1$ and F if B remains in the same direction (FIG. 2b). In order to achieve unidirectional cell migration, the direction of B must also be reversed with the same frequency as $v_1$ (FIG. 2c) to allow F the same direction as in FIG. 2a.

The magnitude of F is deduced as follows. Since $dP/dt = s(dq/dt) + q(ds/dt)$ and $dq/dt = 0$, it follows that $$dP/dt = q(ds/dt) = 2q \cdot v_1 \quad (5)$$

and $F = 1/2(dP/dt \times B)$.

and $F = \frac{1}{2}(dP/dt \times B)$. (5)

The magnetic field applied perpendicular to E must oscillate at the same frequency $\omega$ as the electric field, but 90 degrees out of phase for maximum force F:

$$\vec{B} = B \sin\omega \quad (6)$$

Combining equations 4, 5 and 6 yields:

$$F = -\frac{2\pi\epsilon_o a^3 K}{1 + (\omega\tau)^2} E_o B_o(-\omega\sin\omega t + w^2\tau\cos\omega t \cdot \sin\omega t) \quad (7)$$

The moving cell also experiences friction in the surrounding medium. The resulting force F' is described by Stokes Law:

$$F' = 6\pi\eta v a \quad (8)$$

where
 $\eta$ = absolute viscocity
 v = relative velocity of spheres and liquid
 a = radius of spheres In steady state, 2F = F' and the cell is moving with velocity of magnitude $$v = -\frac{\epsilon_o a^2 k}{3\eta} E_o B_o (-\omega\sin^2\omega t + \omega\tau\cos\omega t \sin\omega t) \quad (9)$$

The average velocity per cycle is obtained by integrating equation (9) over one cycle:

$$<v> = \frac{\omega\epsilon_o a^2 K}{6\eta(1 + (\omega\tau)^2)} E_o B_o. \quad (10)$$

Substituting $\omega = 2\pi f$, $\tau = \frac{1}{2}\pi f_o$, and K=1 in a non-conducting medium, where $f_0$ is the relaxation frequency of the cell, leads to $$<v> = \frac{\epsilon_o f a^2}{3\eta (1 + (f/f_o)^2)} E_o B_o. \quad (11)$$

This relationship describes the average migration velocity as a biphasic function of field frequency. Therefore in the presence of perpendicular, oscillating electric and magnetic fields, a gross cell migration will result, with highest velocity in cells of relaxation frequency closest to the applied frequency, if other factors are equal. In order to recover cells from the medium, various cell collecting systems may be implemented, as will be explained hereafter.

The dielectric constant of an object is a measure of the object's polarizability. It also provides information about the relaxation frequency. Dielectric constants of dry polymers are low. Upon hydration, when absorbed water is above a critical value, the dielectric constants increase drastically. The frequency dependence of the wet dielectric constant has been investigated by others of polystyrene microspheres. Results resemble those displayed by live tissue and cells.

Figure 3A:
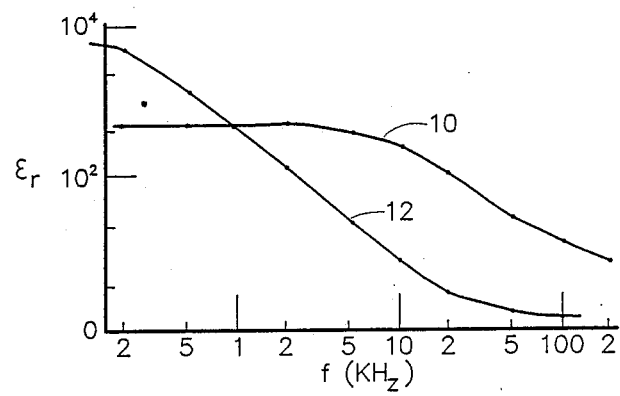
FIGS. 3a, 3b, 3c and 3d are a series of graphs depicting the relationships between the relative dielectric constant $\epsilon_r$ and frequency in experimental tests of the method of the present invention with polystyrene microspheres and different biological particles.

The graph of (FIG. 3a) depicts the relationship between the relative dielectric constant ($\epsilon_r$) and frequency in kilohertz for two suspensions of polystyrene spheres. Curve 10 is for spheres having a diameter of 0.166 micrometers. Curve 12 is for spheres having a diameter of 1.17 micrometers.

Figure 3B:
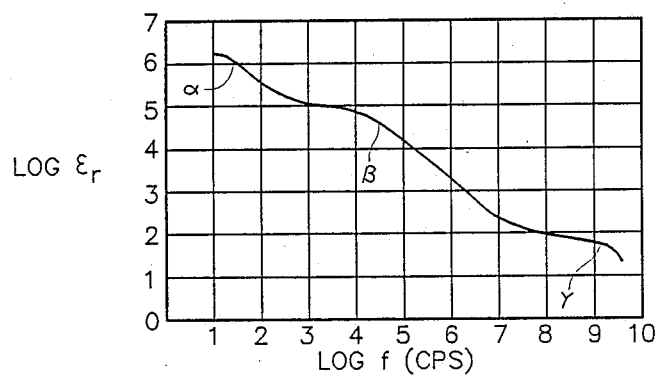

The graph of (FIG. 3b) depicts the relationship of Log $\epsilon_r$ versus Log f(Hz) for muscular tissue in liquid suspension. Three major steps in the decrease are identified as $\alpha$, $\beta$ and $\gamma$.

Figure 3C:
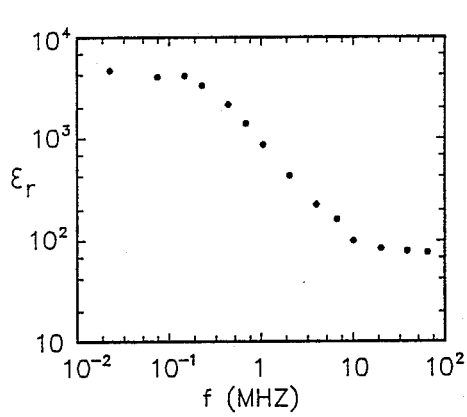

The graph of (FIG. 3c) depicts the relationship of $\epsilon_r$ and frequency for human B lymphocyte cells suspended at 24 degrees C.

Figure 3D:
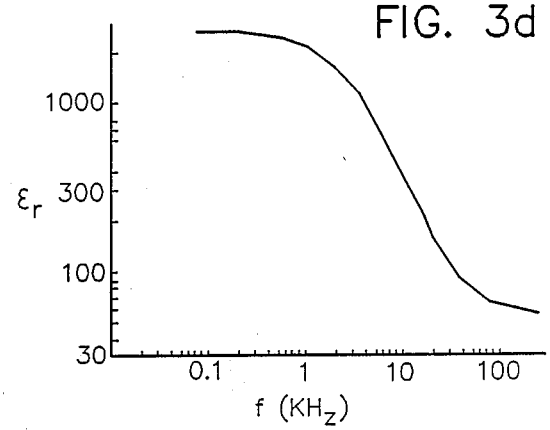

The graph of (FIG. 3d) depicts the relationship of $\epsilon_r$ and frequency for packed human erythrocytes.

The relaxation frequency ($f_o$) may be considered as the frequency at which half maximal dielectric constant was reached in a single step of the frequency-dependent function. Thus f was found to be in the kHz range for polystyrene spheres and MHz range for cells. The similarity in dielectric behavior of the microspheres and live cells suggests a common polarization mechanism. In addition, dielectrophoresis of polystyrene microspheres similar to that exhibited by live cells in nonuniform oscillating electric fields has been demonstrated.

Figure 4:
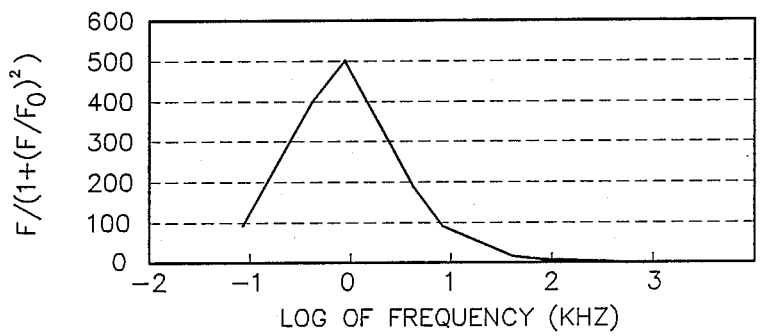
FIGS. 4 and 5 are further graphs illustrating the theoretical prediction of migration velocity as a function of field frequency for polystyrene micropspheres and cells, respectively.
Figure 5:
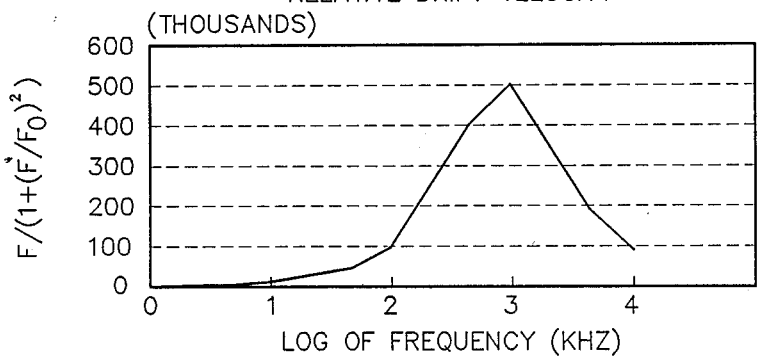

FIGS. 4 and 5 are further graphs illustrating the theoretical prediction of migration velocity as a function of field frequency for polystyrene micropspheres and cells, respectively.

Figure 1:
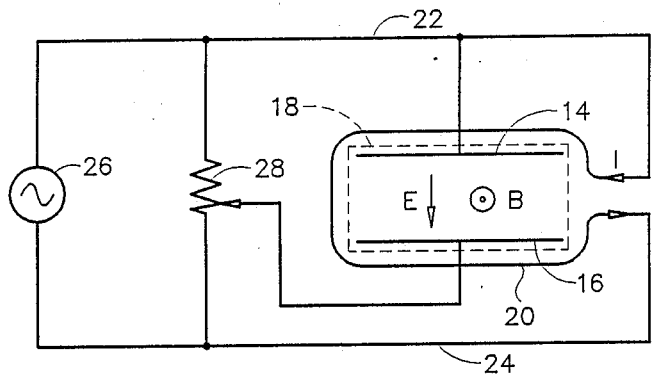
FIG. 1 is a simplified schematic illustration of an apparatus that may be used to perform the method of the present invention.

FIG. 1 illustrates an apparatus suitable for performing the method of the present invention. A pair of electrodes 14 and 16 are supported in spaced apart fashion inside a liquid container 18 illustrated in phantom lines. A coil 20, which may be formed of a plurality of turns of wire, surrounds the container 18. The coil could be insulated and mounted within the container, it being understood that the coil must surround the region between the electrodes 14 and 16. The coil 20 is connected via conductors 22 and 24 to an electric power source 26, such as an alternating current source having a sinusoidal waveform. The electrode 16 is connected to means for providing a variable voltage, such as variance 28 connected across conductors 22 and 24. The other electrode 14 is connected directly to the conductor 22. It will be readily understood that when small dielectric particles are suspended in a quantity of a liquid medium of high resistivity in the container 20, the electrodes will have a first variable voltage signal applied thereto through, and as a result of being immersed in the liquid, the particles will be subjected to an electric field between the electrodes. At the same time, a second signal applied to the coil directly from the power source 26 will cause the surrounding coil 20 to generate a magnetic field that will also affect the particles in liquid suspension. Thus the particles will simultaneously be subjected to orthogonal (perpendicular) oscillating electric and magnetic fields that are ninety degrees out of phase.

In a test device constructed in accordance with FIG. 1, the electrodes consisted of a pair of stainless steel bars spaced approximately 0.5 centimeters apart. The bars were mounted in a plastic container with a rectangular coil consisting of sixty-five turns of copper wire wound thereabout. The electrode area was approximately six and one-half square centimeters. The coil had a height of approximately 1.2 centimeters, and width of approximately 4.5 centimeters and a depth of approximately 14.5 centimeters. The power source was ordinary 110 volt, sixty cycle AC household current. A solution of distilled water and styrene microspheres having a diameter of twenty micrometers was placed in the container. The voltage on the electrodes was adjusted to approximately ten volts peak and the current in the coil was approximately sixteen amps. The electric field strength was approximately 200 volts per centimeter and the magnetic field strength was approximately 200 gauss. The resonance frequency (f) was 1000 1/S. A drift velocity of 0.84 mm/min was observed.

As already indicated, my method and apparatus my be modified to separate biological cells and tissues, and large biological molecules such as DNA and parts of DNA, without destroying the same. It is possible to separate living cells with my invention. For this purpose, it is desirable that the resistivity of the supporting liquid medium be at least about 10,000 ohms per centimeter. This insures that heating will be minimized. Such heating could result damage to the cells or sufficient convection in the liquid to disturb the unidirectional migration. In cell separation, it is preferable that the frequency be between about 0.1 and 10,000 kilohertz. The electric field strength should be at least about 50V/cm and the magnetic field strength should be at least about 100 Gauss. Baffles or other mechanisms may aid in extracting cell fractions from the container.

In using my invention to separate DNA molecules and fragments thereof, a sideways drift is introduced so that the shape or length of the molecule will determine its migration velocity. The frequency of the applied fields may be varied to give insight into the stiffness of the different molecule fragments.

Having described preferred embodiments of a method and apparatus for separating cells, large molecules, which can be charged, and other small particles in liquid suspension utilizing oscillating electric and magnetic fields, it will be apparent to those skilled in the art that my invention may be modified in both arrangement and detail. Therefore the protection afforded my invention should only be limited in accordance with the scope of the following claims.

I claim:

1. A method of separating dielectric particles, comprising the steps of:
   supporting the particles in a fluid medium;
   subjecting the particles to oscillating electric and magnetic fields at substantially the same predetermined frequency;
   the fields being oriented substantially orthogonal to each other and being generated approximately ninety degrees out of phase; and
   the predetermined frequency being selected so that particles having different polarization relaxation frequencies will migrate unidirectionally at different velocities;
   whereby the particles will be sorted into different fractions.

2. A method according to claim 1 wherein the medium is a liquid.

3. A method according to claim 1 wherein the particles are cells and the medium is aqueous.

4. A method according to claim 1 wherein the particles are large molecules.

5. A method according to claim 4 wherein the molecules are selected from the group consisting of DNA and DNA fragments.

6. A method according to claim 2 wherein the liquid is held in a container.

7. A method according to claim 6 wherein the electric field is generated by applying an electric signal to a pair of spaced apart electrodes immersed in the liquid.

8. A method according to claim 6 wherein the magnetic field is generated by applying an electric signal to a coil that surrounds the container.

9. A method according to claim 2 wherein the electric field and the magnetic field are generated by applying a first alternating electric current signal to a pair of spaced apart electrodes immersed in the liquid and by applying a second alternating electric current signal to a coil surrounding the liquid.

10. A method according to claim 9 wherein each of the first and second alternating electric current signals has a sinusoidal waveform.

11. A method according to claim 10 wherein the particles are cells suspended in a liquid and the predetermined frequency is between about 0.1 and 10,000 kilohertz.

12. A method according to claim 11 wherein the strength of the electric field is at least about 50 V/cm.

13. A method according to claim 11 wherein the strength of the magnetic field is at least about 100 Gauss.

14. A method according to claim 2 wherein the resistivity of the liquid is at least 10,000 ohms per centimeter to minimize heating that would result in sufficient convention to disturb the unidirectional migration.

15. A method of separating biological cells, comprising the steps of:
   supporting the cells in a liquid solution having a resistivity of at least 10,000 ohms per centimeter;
   subjecting the to cells to oscillating electric and magnetic fields at substantially the same predetermined frequency of between about 0.1 and 10,000 kilohertz;

the fields being oriented substantially orthogonal to each other and being generated approximately ninety degrees out of phase; and the strength of the fields being selected so that the cells having different polarization characteristics will migrate unidirectionally at different velocities;

whereby the cells will be sorted into different fractions.

16. An apparatus for separating particles in liquid suspension, comprising:

a container for holding the liquid;

a pair of spaced apart electrodes mounted in the container;

a coil surrounding a region between the electrodes; and means for applying first and second electric signals to the electrodes and plates, respectively, to thereby generate substantially orthogonal oscillating electric and magnetic fields which are substantially at the same predetermined frequency but approximately ninety degrees out of phase.

17. An apparatus according to claim 16 wherein the first and second signals have a sinusoidal waveform.

18. An apparatus according to claim 16 wherein the predetermined frequency is between about 0.1 and 10,000 kilohertz.

19. An apparatus according to claim 16 wherein the strength of the electric field is at least about 50 V/cm.

20. An apparatus according to claim 16 wherein the strength of the magnetic field is at least about 100 Gauss.

* * * * *